(12) United States Patent
Parthasaradhi Reddy et al.

(10) Patent No.: US 7,629,482 B2
(45) Date of Patent: Dec. 8, 2009

(54) PROCESS FOR PREPARATION OF CEFPROZIL INTERMEDIATE

(75) Inventors: Bandi Parthasaradhi Reddy, Andhrapradesh (IN); Kura Rathnakar Reddy, Andhrapradesh (IN); Rapolu Raji Reddy, Andhrapradesh (IN); Dasari Muralidhara Reddy, Andhrapradesh (IN); Nagabelli Murali, Hyderabad Andhrapradesh (IN)

(73) Assignee: Hetero Drugs Limited (IN)

( * ) Notice: Subject to any disclaimer, the term of this patent is extended or adjusted under 35 U.S.C. 154(b) by 0 days.

(21) Appl. No.: 12/257,738

(22) Filed: Oct. 24, 2008

(65) Prior Publication Data
US 2009/0048460 A1    Feb. 19, 2009

Related U.S. Application Data

(62) Division of application No. 10/595,544, filed as application No. PCT/IN2004/000337 on Nov. 1, 2004.

(51) Int. Cl.
*C07F 7/10*    (2006.01)
(52) U.S. Cl. .................................. 556/413; 556/423
(58) Field of Classification Search ................ 556/413, 556/423
See application file for complete search history.

(56) References Cited

U.S. PATENT DOCUMENTS

| | | | |
|---|---|---|---|
| 3,940,354 A | 2/1976 | Martel et al. | |
| 3,988,450 A | 10/1976 | James | |
| 4,139,702 A | 2/1979 | Broggi et al. | |
| 4,148,817 A | 4/1979 | Wright | |
| 4,520,022 A | 5/1985 | Hoshi et al. | |
| 4,694,079 A | 9/1987 | Crast, Jr. | |
| 4,727,070 A | 2/1988 | Kaplan et al. | |
| 5,608,055 A | 3/1997 | Diago et al. | |

FOREIGN PATENT DOCUMENTS

| | | |
|---|---|---|
| GB | 2173798 A | 4/1986 |
| JP | 57185291 A2 | 11/1982 |
| WO | 9804732 | 2/1998 |
| WO | 03011871 A2 | 2/2003 |
| WO | 2004083172 A2 | 8/2004 |
| WO | 2006048887 A1 | 5/2006 |

*Primary Examiner*—Elvis O Price
(74) *Attorney, Agent, or Firm*—Caesar, Rivise, Bernstein, Cohen & Pokotilow, Ltd.

(57) ABSTRACT

The present invention relates to a process for preparing a key intermediate of cefprozil and use of this intermediate in the preparation of cefprozil thereby avoiding impurity-causing self-acylation.

[R-(Z)]-[4-hydroxy-α-[(3-methoxy-1-methyl-3-oxo-1-propenyl)amino]] benzeneacetic acid, mono potassium salt is reacted with ethyl chloroformate to obtain mixed anhydride which is then silylated with N,O-bis(trimethylsilyl)acetamide. The silylated compound obtained is reacted with [7-trimethylsilylamino-3-(Z/E-propen-1-yl)-3-cephem-4-carboxylic acid]trimethylsilyl ester and deprotected with aqueous hydrochloric acid to give cefprozil.

11 Claims, No Drawings

PROCESS FOR PREPARATION OF CEFPROZIL INTERMEDIATE

This application is a Divisional of U.S. application Ser. No. 10/595,544 filed Apr. 27, 2006, which is a National Stage Entry of PCT/IN2004/000337 filed Nov. 1, 2004.

FIELD OF THE INVENTION

The present invention relates to a process for preparing a key intermediate of cefprozil and provides less expensive and commercially viable process for preparing cefprozil.

BACKGROUND OF THE INVENTION

U.S. Pat. No. 4,520,022 disclosed 3-[(Z)-1-propen-1-yl]-7-acylamido cephalosporins. These compounds are antibacterial agents. Among them Cefprozil, chemically (6R, 7R)-7-[2-amino-2-(4-hydroxyphenyl)acetamido]-3-[(Z)-propenyl]-3-cephem-4-carboxylic acid is an orally effective cephalosporin antibiotic having a broad spectrum of antibacterial activity against both gram-positive and gram-negative organisms. Cefprozil is represented by the following structure:

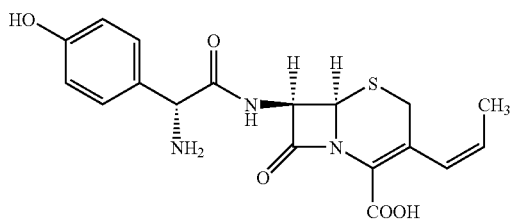

I

Processes for the preparations of cefprozil, it's hydrates and related compounds were described in U.S. Pat. No. 4,727,070, WO 98/04732, U.S. Pat. No. 4,694,079 and GB 2173798. U.S. Pat. No. 4,694,079 disclosed a process for the preparation of DMF solvate of cefprozil. U.S. Pat. No. 5,608,055 disclosed a process for the preparation of 7-α-acylamino-cephalosporin by acylating 7-amino-3-cephem-4-carboxylic acid or a derivative thereof in a halogen-free solvent. According to U.S. Pat. No. 4,148,817 the silylation of [R-(Z)]-[4-hydroxy-α-[(3-methoxy-1-methyl-3-oxo-1-propenyl) amino]]benzeneacetic acid, mono potassium salt (amoxydane salt) can be done properly with hexamethyldisilazane and trimethylsilyl iodide and the silylated salt is converted into a mixed anhydride; and the patent also disclosed that the use of N,O-bis(trimethylsilyl)acetamide in the silylation results in the development of color which cannot be removed. Moreover the process as per U.S. Pat. No. 4,148,817 requires isolation of silylated amoxydane salt intermediate before converting to silylated anhydride.

All the aforesaid patents are incorporated herein by reference.

DETAILED DESCRIPTION OF THE INVENTION

According to one aspect of the present invention, there is provided a process for preparing silylated mixed anhydride of formula II:

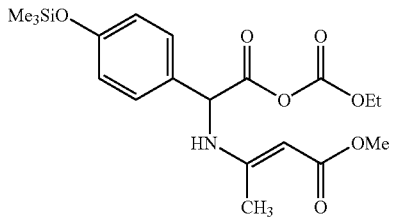

II which comprises reacting the compound of formula III or a salt thereof:

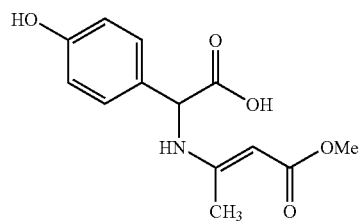

III with ethyl chloroformate of formula IV:

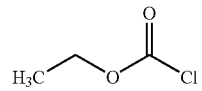

IV to obtain mixed anhydride of formula V:

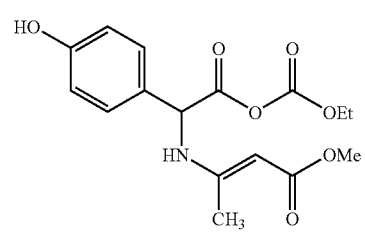

V then silylating the mixed anhydride of formula V obtained above with N,O-bis(trimethylsilyl)acetamide to obtain the compound of formula II:

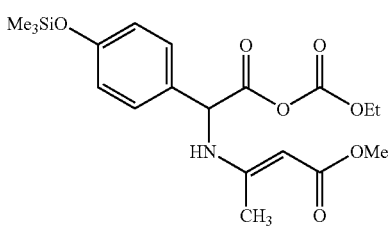

II

Mixed anhydride of formula V can be prepared by reacting the compound of formula III or a salt thereof with ethyl chloroformate in an organic solvent such as a chlorinated solvent, optionally in the presence of another solvent such as dimethylformamide. Preferably, catalytic quantities of N-methyl morpholine and methanesulfonic acid may also be used.

The reaction is carried out below about −20° C., preferably below about −40° C.

Silylation of the mixed anhydride is carried out in an organic solvent such as a chlorinated solvent using N,O-bis(trimethylsilyl)acetamide. Other common silylating reagents such as hexamethyldisilazane and trimethylsilyl iodide etc., failed to silylate the anhydride. This is contrary to the observation (U.S. Pat. No. 4,148,817) that silylation of [R-(Z)]-[4-hydroxy-α-[(3-methoxy-1-methyl-3-oxo-1-propenyl)amino]]benzeneacetic acid, mono potassium salt (amoxydane salt) can be done properly with hexamethyidisilazane and trimethylsilyl iodide and the use of N,O-bis(trimethylsilyl)acetamide results in the development of color which cannot be removed. Thus, silylation of amoxydane salt is different from the silylation of the mixed anhydride of formula II.

Moreover, the novel process does not require isolation of intermediates whereas the prior art process (U.S. Pat. No. 4,148,817) requires isolation of silylated amoxydane salt intermediate before converting to silylated anhydride.

The compound of formula III used as starting material is commercially available.

Use of silylated mixed anhydride of formula II in the preparation of cefprozil and pharmaceutically acceptable salts thereof is also novel and provides another aspect of the present invention. Cefprozil and pharmaceutically acceptable salts also include their hydrates or solvates. The use of the silylated compound of formula V in the preparation of cefprozil is known but the problem with the use of the compound is the self-acylation resulting in the formation of the corresponding impurity. So, this requires strict control of relative quantity of this compound and strict control of addition of the compound to the compound of formula VI in order to avoid the self-acylation. The use of the silyl protected compound of formula II avoids the self-acylation and so, strict control of quantity of silyl protected intermediate is not required and controlled addition of the reactant is not required; and so, the use of the silyl protected compound of formula II in the preparation of cefprozil is practically advantageous. The use of formula II in the preparation of cefprozil may be formulated in the scheme shown below.

Scheme:

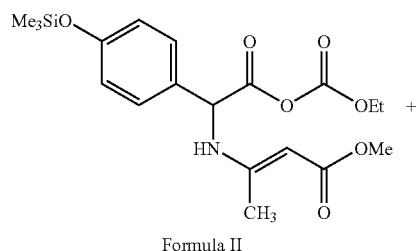

Formula II

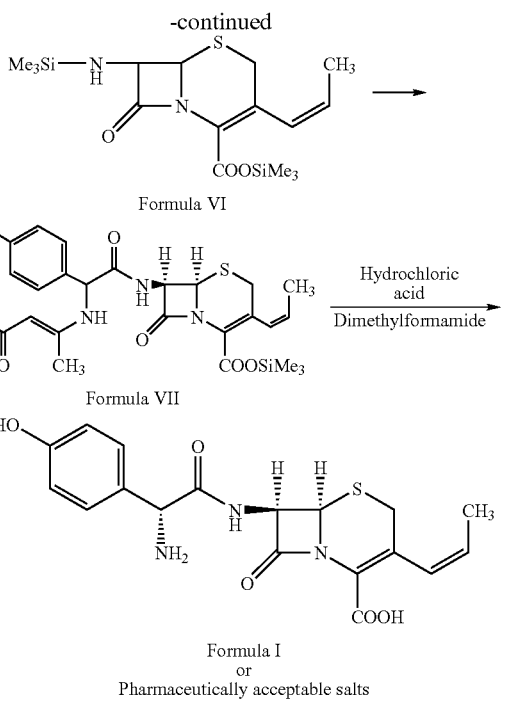

The reaction between the silylated compound of formula II and the compound of formula VI is carried out in chlorinated solvents such as methylene chloride. Preferably the reaction is carried out at −50° C. to 40° C., more preferably at −40° C. to 25° C.

It has been found that the silylated mixed anhydride of formula II does not react with compound of formula VI in solvents such as acetonitrile or hydrocarbon solvent such as cyclohexane.

The deprotection of silyl protected and N-protected group of the compound of formula VII obtained above may preferably be carried out with aqueous hydrochloric acid solution to obtain compound of formula I.

Compound of formula I (cefprozil) may be isolated and converted to hydrates, solvates and pharmaceutically acceptable salts by known methods.

The compound of formula I is preferably precipitated from the reaction mass as dimethylformamide solvate (cefprozil DMF solvate) by adjusting the pH of the reaction mass to about 5.5 to 7.0 with a base such as ammonia in the presence of dimethylformamide.

Cefprozil DMF solvate may be converted to cefprozil hydrates or solvates; or to a pharmaceutically acceptable salt by a known method.

The compound of formula VI used as starting materials may be prepared by known methods for example as described in U.S. Pat. No. 4,694,079.

The invention will now be further described by the following examples, which are illustrative rather than limiting.

PREPARATIVE EXAMPLE 1 p-Methoxybenzyl 7-phenylacetamido-3-chloromethyl-3-cephem-4-carboxylate (100 gm) is suspended in a mixture of methylene chloride (600 ml) and water (600 ml), then sodium iodide (32.32 gm) and triphenylphosphine (56.5 gm) are added at 25° C. and the contents are stirred for 1 hour 30 minutes at 25° C. Then the layers are separated, the resulting organic layer is cooled to 0° C. and then 1.5% sodium hydroxide solution (600 ml) is added. The contents are stirred for 1 hour at 0° C., separated the layers and washed the resulting organic layer with saturated sodium chloride solution (2 L). Then the organic layer is cooled to −10° C., isopropyl alcohol (700 ml), water (500 ml) and acetaldehyde (90.65 gm) are added and stirred for 20 hours. The reaction mass is treated with sodium metabisulfite, stirred for 10 minutes and separated. Distilled off methylene chloride, isopropyl alcohol (400 ml) and water (200 ml) are added to the reaction mass and stirred for 2 hours at 0-5° C. Then the separated solid is filtered and dried under vacuum to give 70 gm of p-methoxybenzyl 7-phenylacetamido-3-(Z/E-propen-1-yl)-3-cephem-4-carboxylate.

PREPARATIVE EXAMPLE 2

Phosphorous pentachloride (136 gm) is added to methylene chloride (625 ml) at 25° C. to 30° C., cooled to 15° C. under $N_2$ atmosphere and then pyridine (45 gm) is added for 30 minutes at 15-20° C. The contents are stirred for 5 minutes, cooled to −12° C. and then stirred for 20 minutes at −12° C. Then p-Methoxybenzyl 7-phenylacetamido-3-(Z/E-propen-1-yl)-3-cephem-4-carboxylate (125 gm, obtained as in example 2) is added to the reaction mass at −12° C., stirred for 1 hour 30 minutes at −12° C. and then cooled to −25° C. 1,3-Propanediol (125 ml) is added to the reaction mass for 30 minutes at −25° C., stirred for 30 minutes at −25° C. and phenol (500 gm) in methylene chloride (125 ml) is added at −25° C. The reaction mass is stirred for 2 hours at −25° C. to −15° C., water (500 ml) is added at −15° C. to −10° C. and stirred for 15 minutes. Then separated the layers and the organic layer is extracted with 2N HCl (2 L). The total aqueous layer is washed with methylene chloride (500 ml), pH is adjusted to 2.0 with 25% sodium hydroxide at 0-5° C. and stirred for 1 hour at the same temperature. Then the separated solid is filtered and washed with acetone (250 ml) to give 41.25 gm of 7-Amino-3-(Z/E-propen-1-yl)-3-cephem-4-carboxylic acid (containing 8.8% E-isomer).

EXAMPLE

Step-I:

To a slurry of 7-Amino-3-(Z/E-propen-1-yl)-3-cephem-4-carboxylic acid (30 gm, obtained as in preparative example 2) in methylene chloride (120 ml) is added hexamethyl disilazane (19.8 ml), trimethyl chlorosilane (12.6 ml) and imidazole (300 mg) and the contents are heated to reflux for 4 hours. Then the resulting solution is cooled to −15° C. under nitrogen atmosphere to give [7-trimethylsilylamino-3-(Z/E-propen-1-yl)-3-cephem-4-carboxylic acid] trimethylsilyl ester.

Step-II:

Methylene chloride (180 ml) is added to [R-(Z)]-[4-hydroxy-α-[(3-methoxy-1-methyl-3-oxo-1-propenyl)amino]]benzeneacetic acid, mono potassium salt (43.5 gm), cooled to −20° C. and dimethylformamide (160 ml) is added at −20° C. Then methanesulfonic acid (0.4 ml) and N-methylmorpholine (0.44 ml) are added. The contents are cooled to −50° C. to −60° C., ethyl chloroformate (14 ml) is added and stirred for 1 hour 30 minutes. N,O-bis(trimethylsilyl)acetamide (39 ml) is added to the reaction mass, stirred for 30 minutes and [7-trimethylsilylamino-3-(Z/E-propen-1-yl)-3-cephem-4-carboxylic acid]trimethylsilyl ester obtained in step-I is added to this solution. The contents are stirred for 3 hours, 2N hydrochloric acid (120 ml) is added and the layers are separated. Then the mixture of dimethylformamide (300 ml) and acetone (75 ml) is added to the reaction mass, carbon (3 gm) is added and stirred for 30 minutes. Filtered the reaction mass, washed with 150 ml of dimethylformamide and the pH is adjusted to 6-6.5 with $NH_3$ solution. Then the precipitated solid is filtered, washed with dimethylformamide and acetone and dried under vacuum at 40° C. to give 58 gm of cefprozil dimethylformamide solvate (1.5 mole dimethylformamide per mole of cefprozil.

Step-III:

The mixture of Cefprozil dimethylformamide solvate (58 gm, obtained in step-II) and water (100 ml) is stirred for 1 hour, filtered, washed with acetone (100 ml) and dried under vacuum at 40-45° C. to give 40 gm of cefprozil monohydrate (containing 10% E-isomer).

We claim:
1. A process for preparing silylated mixed anhydride of formula II:

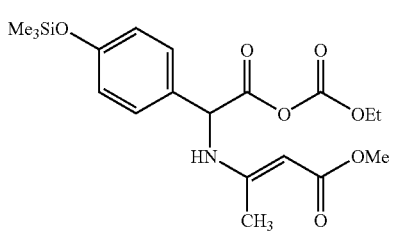

which comprises reacting the compound of formula III or a salt thereof:

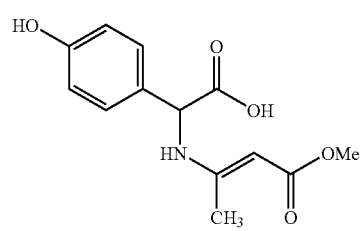

with ethyl chloroformate of formula IV:

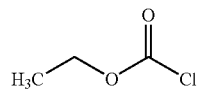

to obtain mixed an hydride of formula V:

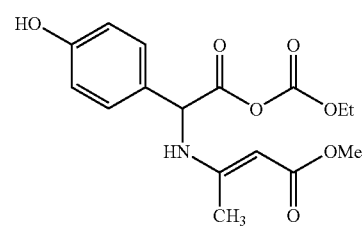

then silylating the mixed anhydride of formula V obtained above with N,O-bis(trimethylsilyl)acetamide to obtain the compound of formula II.

2. The process according to claim 1, wherein the mixed anhydride of formula V is prepared by reacting [R-(Z)]-[4-hydroxy-α-[(3-methoxy-1-methyl-3-oxo-1-propenyl)amino]]benzeneacetic acid, mono potassium salt (amoxydane salt) with ethyl chloroformate in a chlorinated solvent.

3. The process according to claim 2, wherein the chlorinated solvent is methylene chloride.

4. The process according to claim 2, wherein the reaction is carried out in the presence of dimethylformamide along with the said chlorinated solvent.

5. The process according to claim 2, wherein the catalytic quantities of N-methyl morpholine and methanesulfonic acid are used.

6. The process according to claim 1, wherein the reaction between the compound of formula III or salt thereof and ethyl chloroformate is carried out below about −20° C.

7. The process according to claim 6, wherein the reaction is carried out below −40° C.

8. The process according to claim 1, wherein the silylation of the mixed anhydride is carried out in a chlorinated solvent.

9. The process according to claim 8, wherein the chlorinated solvent is methylene chloride.

10. The process according to claim 3, wherein the catalytic quantities of N-methyl morpholine and methanesulfonic acid are used.

11. The process according to claim 4, wherein the catalytic quantities of N-methyl morpholine and methanesulfonic acid are used.

* * * * *